United States Patent
Liu

(10) Patent No.: US 6,960,592 B2
(45) Date of Patent: Nov. 1, 2005

(54) 1,6-DIHYDRO-7H-PYRAZOLO[4,3-D] PYRIMIDIN-7-ONE COMPOUND FOR THE TREATMENT OF IMPOTENCE

(76) Inventor: Baoshun Liu, Rm 101, No. 10 Dong Sheng Yuan, Cheng Fu Rd., Haidian District, Beijing 100083 (CN)

( * ) Notice: Subject to any disclaimer, the term of this patent is extended or adjusted under 35 U.S.C. 154(b) by 12 days.

(21) Appl. No.: 10/736,732

(22) Filed: Dec. 16, 2003

(65) Prior Publication Data

US 2004/0152709 A1 Aug. 5, 2004

Related U.S. Application Data

(63) Continuation of application No. PCT/CN02/00433, filed on Jun. 21, 2002.

(30) Foreign Application Priority Data

Jun. 29, 2001 (CN) .......................................... 01129691
Jan. 18, 2002 (CN) .......................................... 02100198

(51) Int. Cl.⁷ .................... C07D 478/04; C07D 403/12; A61K 31/519; A61P 15/10
(52) U.S. Cl. ...................... 514/262.1; 544/256; 544/371
(58) Field of Search ....................... 514/262.1; 544/256, 544/371

(56) References Cited

U.S. PATENT DOCUMENTS

| | | | |
|---|---|---|---|
| 5,250,534 A | * | 10/1993 | Bell et al. .............. 514/252.16 |
| 5,955,611 A | | 9/1999 | Dunn et al. ................. 544/262 |
| 6,200,980 B1 | * | 3/2001 | Piazza et al. .......... 514/252.16 |
| 6,469,012 B1 | | 10/2002 | Ellis et al. ............... 514/234.5 |

FOREIGN PATENT DOCUMENTS

| | | |
|---|---|---|
| CN | 1124926 | 6/1996 |
| CN | 1168376 A | 12/1997 |
| EP | 0 463 756 A1 | 1/1992 |

OTHER PUBLICATIONS

PCT International Search Report, International Application No. PCT/CN02/00433; dated: Dec. 12, 2002, pp. 1–3.

* cited by examiner

Primary Examiner—Thomas C. McKenzie
(74) Attorney, Agent, or Firm—Palmer & Dodge LLP; Kathleen M. Williams

(57) ABSTRACT

The present invention relates to new 1,6-dihydro-7H-pyrazolo[4,3-d]pyrimidin-7-one compounds of formula (I), or a pharmaceutically acceptable salt or a stereoisomer thereof, useful for treatment of impotence diseases:

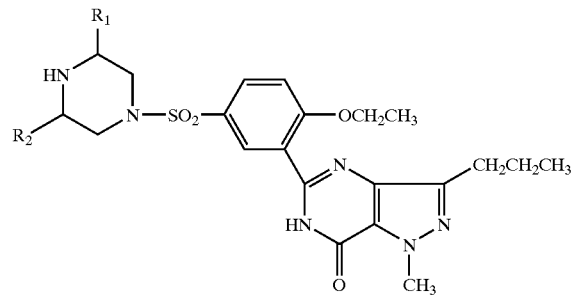

wherein $R_1$ and $R_2$ may be the same or different and independently be $C_{1-6}$ alkyl. The present invention also provides a method of preparing the compounds of formula (I).

8 Claims, No Drawings

1,6-DIHYDRO-7H-PYRAZOLO[4,3-D] PYRIMIDIN-7-ONE COMPOUND FOR THE TREATMENT OF IMPOTENCE

This application is a continuation of the National Stage of International Application No. PCT/CN02/00433, filed on Jun. 21, 2002, which designated the United States and was published in Chinese, which claims the benefit of Chinese Patent Application No. 01129691.7 filed on Jun. 29, 2001, and Chines Patent Application No. 02100198.7 filed on Jan. 18, 2002. The entire teachings of the above applications are incorporated herein by reference.

TECHNICAL FIELD

This invention relates to new compounds for the treatment of impotence. In particular, the present invention relates to new compounds for the treatment of impotence, their preparation method and their use.

BACKGROUND OF THE INVENTION

Sildenafil is a selective inhibitor of phosphodiesterase whose chemical name is 1-[4-ethoxy-3-(6,7-dihydro-1-methyl-7-oxo-3-propyl-1H-pyrazolo[4,3-d]pyrimidin-5-yl) phenylsulphonyl]-4-methylpiperazine. This compound and its preparation method as well as its use in treating cardiovascular diseases was disclosed in CN1124926A; CN1057464A disclosed the use of this compound in preparing medicine for treating erection dysfunction of male animals. CN1168376A disclosed a new method for preparing sildenafil. CN1246478A disclosed another method for preparing sildenafil. Although sidenafil is very effective on treating male erectile dysfunction, the compound has strong t toxicity and side effects.

SUMMARY OF THE INVENTION

The present invention provides a new selective inhibitor of phosphodiesterase, i.e. the compound as described in formula (I) and its pharmaceutically acceptable salts or its stereoisomers. Such compound has the structure of formula (I):

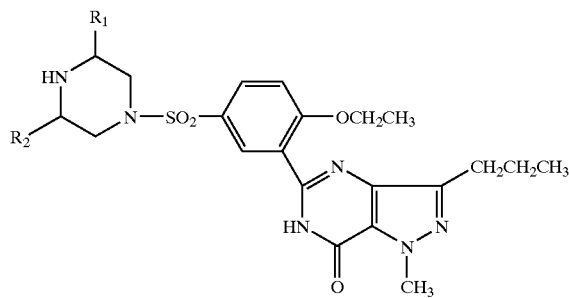

Wherein, $R_1$ and $R_2$ may be the same or different, and independently be $C_{1-6}$ alkyl, and preferably methyl, more preferably, $R_1$ and $R_2$ are both in the cis-form of piperazine ring and are both methyl.

Another object of the present invention is to provide a method for preparing the compound of formula (I).

There are some new intermediates involved in the synthetic route of the present invention. Therefore, another object of the invention is to provide intermediates for preparation of compounds of formula (I).

Still another object of the invention is to provide a pharmaceutical composition having the compound of formula (I) as active component.

Another object of the invention is to provide the use of the compounds of formula (I) as medicine for the treatment of impotence diseases.

According to the present invention, there are two substituted groups, $R_1$ and $R_2$, and two asymmetrical carbon atoms on piperazine ring of the compounds of formula (I). $R_1$ and $R_2$ can be in cis- or trans-form of the piperazine ring. Therefore, the compounds of formula (I) are presented as various stereoisomers. These isomers alone and existing in pharmaceutically acceptable salts, are all within the scope of compounds of the present invention.

Preferably, the compound of the present invention is the compounds of formula (I) wherein $R_1$ and $R_2$ are in the cis-form, and most preferably is the compound wherein $R_1$ and $R_2$ are both methyl and in cis-form, the chemical name of which is: 5-[[2-ethoxy-5-(cis-2,6-dimethylpiperazin-4-ylsulphonyl)phenyl]]-1-methyl-3-n-propyl-7,6-dihydro-1H-pyrazolo[4,3-d]pyrimidin-7-one, i.e., the compound having the structure of formula (I'):

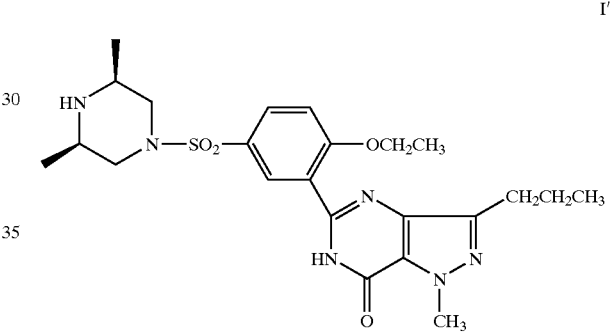

The compound of formula (I) of the present invention is not only effective for the treatment of impotence diseases, such as male erectile dysfunction, but also have such features as long-lasting medical effectiveness and lower toxicity.

The following shows a method of preparing the compound of formula (I'), which is a non-limiting example of preparing compound of formula (I).

The synthetic route of the compounds of formula (I') of the present invention is illustrated as follows:

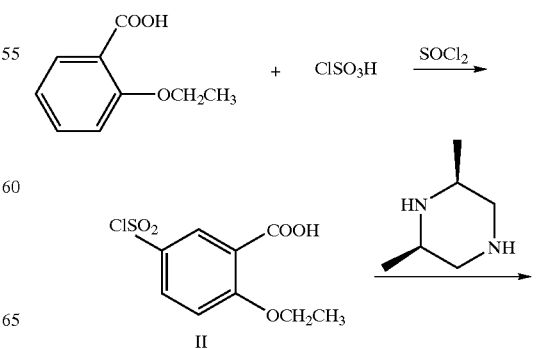

-continued

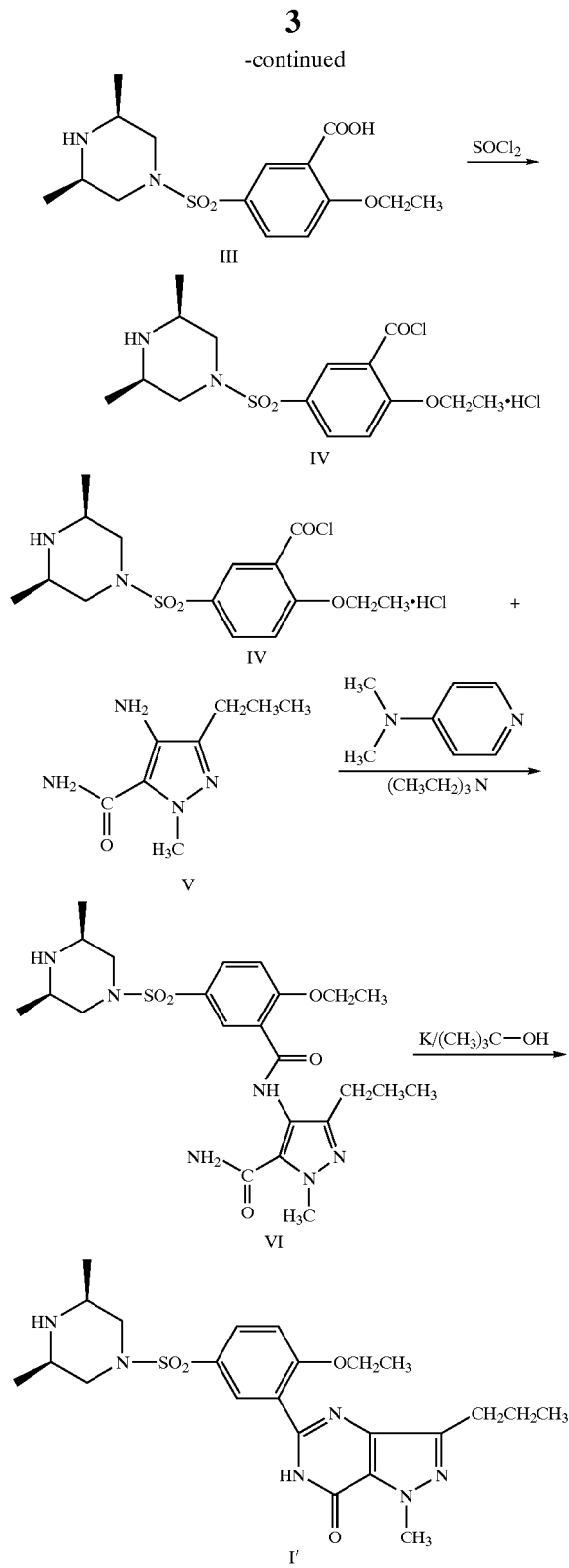

The compound of formula (I') was prepared as follow: reacting 2-ethoxy benzoic acid as raw materials with chlorosulfonic acid in the presence of thionly chloride, results in 5-chlorosulphonyl-2-ethoxy benzoic acid (compound II). Reacting compound II with cis-2,6-dimethyl piperazine (see, Zhongguo Yiyao Gongye Zazhi, 1997, vol. 28(11), page 524–525), results in 2-ethoxy-5-(cis-2,6-dimethylpiperazin-4-yl-sulphonyl) benzoic acid (compound III). Nucleophilic acyl substitution of compound (III) results 2-ethoxy-5-(cis-2,6-dimethylpiperazin-4-ylsulphonyl) benzoyl chloride (compound IV), which is a new compound. Reacting compound IV with compound V (see the synthesis method of the compound of formula IX in CN1246478A), in the presence of 4-dimethylaminopyridine and triethylamine, obtained 4-[[2-ethoxy-5-(cis-2,6-dimethylpiperazin-4-ylsulphonyl)benzamido]]-1-methyl-3-n-propylpyrazole-5-carboxamide(compound VI), which is a new compound. Cyclization of compound VI in the presence of potassium t-butoxide, results 5-[[2-ethoxy-5-(cis-2,6-dimethylpiperazin-4-ylsulphonyl)phenyl]]-1-methyl-3-n-propyl-7,6-dihydro-1H-pyrazolo[4,3-d]pyrimidin-7-one (compound I', (formula (I'))).

DETAILED DESCRIPTION OF THE INVENTION

The method for preparing the compounds of formula (I') of the present invention and their pharmaceutically acceptable salts is hereinafter described by examples. It should be understood that the examples of the preparation methods are only for the purpose of illustrating the present invention and the invention is not limited to the examples. Any modifications under the concept of the present invention to the preparation methods of the present invention fall under the scopes of the present invention.

EXAMPLE 1

Preparation of 5-chlorosulphonyl-2-ethoxy benzoic acid (II)

In a 250 ml three-neck flack, 2-ethoxy benzoic acid (50 g, 0.30 mol) was added dropwise to an ice-cooled mixtures of sulfoxide dichloride (22 ml, 0.30 mol) and chlorosulfonic acid (82.6 ml, 1.24 mol) under stirring. At the same time, the temperature of the reacting mixture was kept below 25° C. The resulting mixture was stirred at room temperature for 18 hours and then poured into ice water with stirring, and white deposit appeared. The reaction mixture was stirred for another 1 hour, filtered, washed with water, and dried in vacuum, which gave 64.4 g of crude product as white solid (II) (yield 81%). m.p. 108–110° C. The crude product was used directly in the next step without further purification.

EXAMPLE 2

Preparation of 2-ethoxy-5-(cis-2,6-dimethypiperazin-4-ylsulphonyl) benzoic acid (III)

In a 250 ml three-neck flask, 52.6 g (0.23 mol) of cis-2,6-dimethylpiperazine was added to the suspension of compound (II) (53 g, 0.20 mol) in water (170 ml) at about 10° C. with stirring, at the same time the temperature of reacting mixture was kept below 20° C. The reaction was then stirred at 10° C. for another 2 hours. The precipitate was filtered, ice-water washed, dried, and refluxed in acetone for 1 hour, and purified, gave 48 g compound (III) (yield 70%) as white crystalline, m.p. 260.5–273.0° C. (Dec.). HNMR (DMSO) δ: 7.72–7.75(2H, H-4 and H-6 on benzene ring), 7.26–7.28(1H, H-3 on benzene ring), 4.12–4.17(2H, —CH$_2$— on —OCH$_2$CH$_3$), 3.5–3.53(2H, —CH$_2$— on piperazine ring), 2.89–2.92(2H, —CH— on piperazine ring), 1.80–1.86(2H, —CH$_2$— on piperazine ring), 1.31–1.34(3H, —CH$_3$ on —OCH$_2$CH$_3$), 1.0–1.04(6H, two —CH$_3$ groups on piperazine ring).

EXAMPLE 3

Preparation of 2-ethoxy-5-(cis-2,6-dimethylpiperazin-4-ylsulphonyl) benzoyl chloride (IV)

Compound (III) (34.2 g, 0.1 mol) and sulfoxide dichloride (73.0 ml, 0.5 mol) were added to a 250 ml three-neck flask and the resulting mixture was heated under reflux for 3 hours. The unreacted sulfoxide dichloride was then evaporated under reduced pressure. The ethyl acetate was added into the residue, and stirred. The precipitate was filtered, washed with ethyl acetate, dried under vacuum. The reaction gave rise to 29.4 g (74%) compound (IV) as a yellow solid. m.p., 206.0–209.5° C. HNMR($D_2O$) δ: 8.0(1H, H-6 on benzene), 7.74–7.76(1H, H-4 on benzene), 7.14–7.16(1H, H-3 on benzene), 4.08–4.11(2H, —$OCH_2$—), 3.74–3.77 (2H, —$CH_2$— on piperazine ring), 3.32(2H, two —CH— 's— on piperazine ring), 2.19–2.25(2H, —$CH_2$— on piperazine ring), 1.24–1.27(3H, —$CH_3$ on —$OCH_2CH_3$), 1.09–1.10(6H, two —$CH_3$ groups on piperazine ring).

EXAMPLE 4

Preparation of 4-[-2-ethoxy-5-(cis-2,6-dimethylpiperazin-4-ylsulphonyl) benzamide]-1-methyl-3-n-propyl pyrazole-5-carboxamide(VI)

125 ml of methylene chloride, 9.1 g (0.05 mol) of 1-methyl-4-amino-3-n-propyl pyrazole-5-formamide (V), 0.06 g (0.0005 mol) of 4-dimethylaminopyridine and 10.1 g (0.1 mol) of triethylamine were added in this order to a 500 ml three-neck flask, and then the mixture was cooled to below 10° C. with cold water. The compound (IV) (25.80 g, 0.065 mol) in methylene chloride (125 ml) solution was added dropwise into the mixture and then stirred at this temperature for 2 hours. The solvent was evaporated, then water was added to the residue. The solid was filtered and washed with ethyl acetate, gave 19.2 g compound (VI) as a grey-white solid, m.p. 197–198.5° C. (yield 76%). HNMR ($CDCl_3$) δ: 8.62(1H, H-6 on benzene ring), 7.90–7.92(1H, H-4 on benzene ring), 7.90(1H, —CO—NH—), 7.17–7.27 (1H, H-3 on benzene ring), 5.73(1H, —NH— on piperazine ring), 4.37–4.41(2H, —$OCH_2CH_3$), 4.06(3H, N—$CH_3$ on pyrazol ring), 3.63–3.66(2H, —$CH_2$— on piperazine ring), 3.0(2H, —CH— on piperazine ring), 2.52–2.56(2H, the first $CH_2$ of —$CH_2CH_2CH_3$), 1.84–1.90(2H, —$CH_2$— on piperazine ring), 1.65–1.69(2H, the second CH2 of —$CH_2CH_2CH_3$), 1.58–1.63(3H, —$OCH_2CH_3$), 1.03–1.05 (6H, —$CH_3$ on piperazine ring), 0.94–0.97(3H, —$CH_2CH_2CH_3$).

EXAMPLE 5

Preparation of 5-[[2-ethoxy-5-(cis-2,6-dimethylpiperazin-4-ylsulphonyl)phenyl]]-1-methyl-3-n-propyl-7,6-dihydro-1H-pyrazolo[4,3-d]pyrimidin-7-one (I')

In a 250 ml three-neck flask, 1.8 g (0.046 mol) of metallic potassium and 96 ml of dry tert-butyl alcohol were added, then to the mixture 19 g (0.0387 mol) of compound (VI) was added. The mixture was heated to reflux with stirring for 8 hours, then cooled to room temperature. 96 ml of water was added and the pH was adjusted to 7.0 by adding 0.5 mol/l of hydrochloric acid, giving precipitate and then standing for 1 hour at a temperature below 10° C. The precipitate was filtered, washed with ice-water, dried and gave 17.0 g compound (I') (yield 93%) as white crystalline. m.p. 202.2–203.2° C. HNMR(McOD) δ: 8.15(1H, H-6 on benzene ring), 7.90–7.93(1H, H-4 benzene ring), 7.36–7.38(1H, H-3 on benzene ring), 4.32(2H, —$OCH_2$—), 4.23(3H, N—$CH_3$), 3.75–3.78(2H, —$CH_2$— on piperazine ring), 3.10(2H, —CH— on piperazine ring), 2.86–2.89(2H, —$CH_2CH_2CH_3$), 2.04–2.10(2H, —$CH_2$— on piperazine ring), 1.80–1.84(2H, —$OCH_2CH_3$), 1.45–1.48(3H, —$OCH_2CH_3$), 1.14–1.17(6H, —$CH_3$ on piperazine ring), 0.97–1.01(3H, —$CH_2CH_2CH_3$). If necessary, the compound of formula (I') may be converted into its pharmaceutically acceptable salts and compositions by conventional method.

The inventors of the present invention discovered that the compounds of the present invention are very effective for treating male erectile dysfunction diseases and have low toxicity and side effects. Specific results of pharmacodynamics and toxicity test are summarized as follows:

EXAMPLE 6

Pharmacodynamics Test

Test 1. Penis erection test of the compound formula (I') in rats with testis removed The result indicates that the latent period of penis erection by electric irritation (10V) can be significantly shortened (P<0.05 and P<0.01) in rats administered the compound formula (I') at the dosage of 24 mg/kg and 12 mg/kg, respectively. This result is the same as another compound sildenafil (P<0.01).

Test 2. Effect of the compound of formula (I') on the sexual function in mice with testis removed Result a. The result shows that latent period which male mice catch female mice can be significantly shortened (P<0.05 and P<0.01) after administration of the compound of formula (I') at the dosage of 24 mg/kg and 12 mg/kg, respectively.

Result b. The result shows that the times of back-climbing on female mice by male mice (times of sexual intercourse) can be significantly increased (P<0.05 and P<0.01) when the male mice was administrated the compound formula (I') at the dosage of 24 mg/kg and 12 mg/kg, respectively.

EXAMPLE 7

Toxicity Test

It was observed by using Bliss method that the half-lethal dosage ($LD_{50}$) is 901.5 mg/kg when mice were administrated the compound formula (I') orally by gavage. The confidence limit of 95% is 772.5–1052.1 mg/kg.

According to the "Chinese Journal of Clinical Pharmacology and Therapeutics", 1999, 4(3), 237–240, the $LD_{50}$ of the compound sidenafil is 625 mg/kg when male mice were administrated orally in the single dose, and the confidence limit of 95% is 50–672 mg/kg.

What is claimed is:

1. A compound of formula (I), or a pharmaceutically acceptable salt or a stereoisomer thereof:

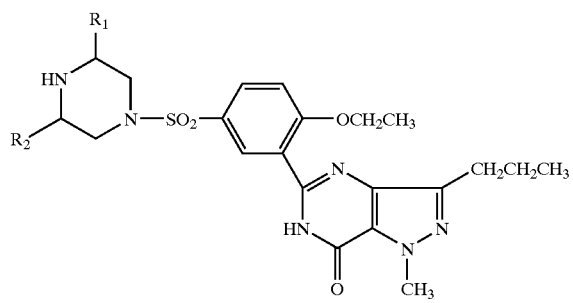

I

Wherein, $R_1$ and $R_2$ may be the same or different and independently be $C_{1-6}$ alkyl.

2. The compound according to claim 1, wherein said compound is 5-[[2-ethoxy-5-(cis-2,6-dimethypiperazin-4-ylsulphonyl)phenyl]]-1-methyl-3-n-propyl-7,6-dihydro-1H-pyrazolo[4,3-d]pyrimidin-7-one, and said compound has the structure of formula (I') as follows:

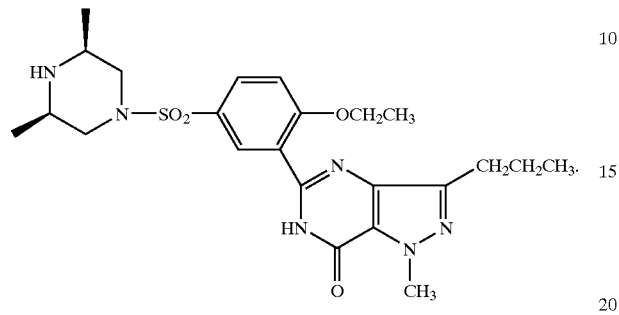

3. A method for preparing the compound of formula (I'), comprising the following steps:

a. reacting 2-ethoxy benzoic acid, as raw materials, with chlorosulfonic acid in the presence of sulfoxide dichloride, obtaining 5-chlorosulphonyl-2-ethoxy benzoic acid (compound II);

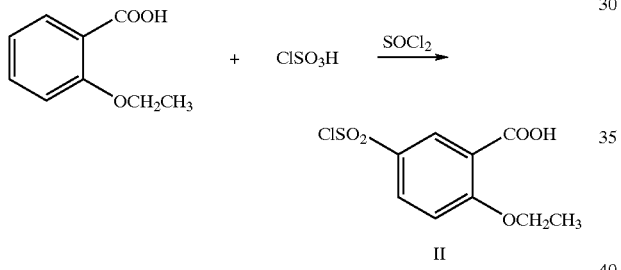

b. reacting the compound II with cis-2,6-dimethyl piperazine, obtaining 2-ethoxy-5-(cis-2,6-dimethyl piperazin-4-ylsulphonyl) benzoic acid (compound III);

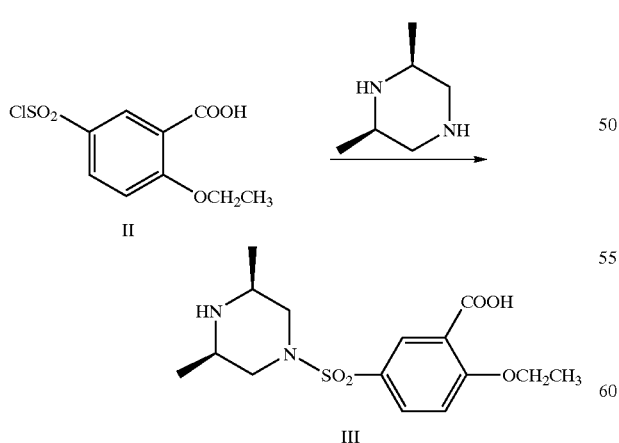

c. nucleophilicacyl substitution of the compound III, obtaining 2-ethoxy-5-(cis-2,6-dimethylpiperazin-4-ylsulphonyl)benzoylchloride(IV);

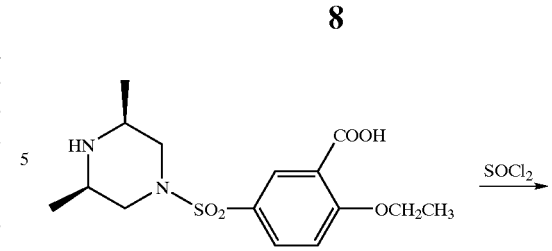

d. reacting the compound (IV) with the compound (V) in the presence of 4-dimethylaminopyridine and triethylamine, obtaining 4-[2-ethoxy-5-(cis-2,6-dimethylpiperazin-4-ylsulphonyl)benzamido]-1-methyl-3-n-propylpyrazole-5-carboxamide (compound VI);

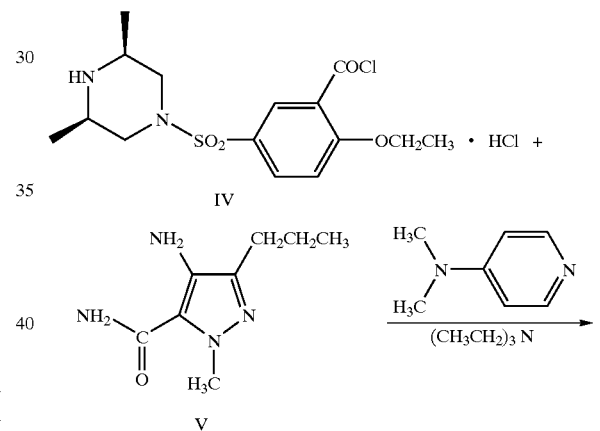

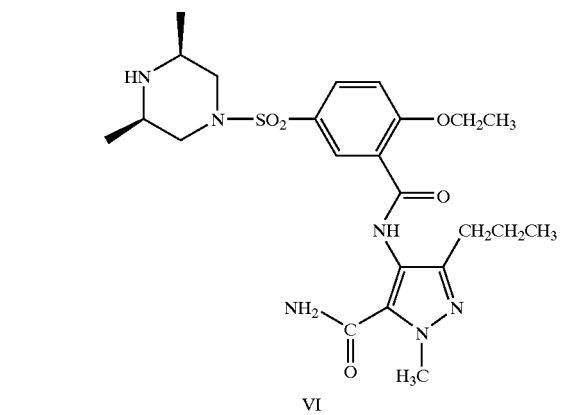

e. cyclization of the compound VI in the present of potassium t-butoxide, obtaining 5-[[2-ethoxy-5-(cis-2,6-dimethylpiperazin-4-ylsulphonyl)phenyl]]-1-methyl-3-n-propyl-7,6-dihydro-1H-pyrazolo[4,3-d]pyrimidin-7-one (I')

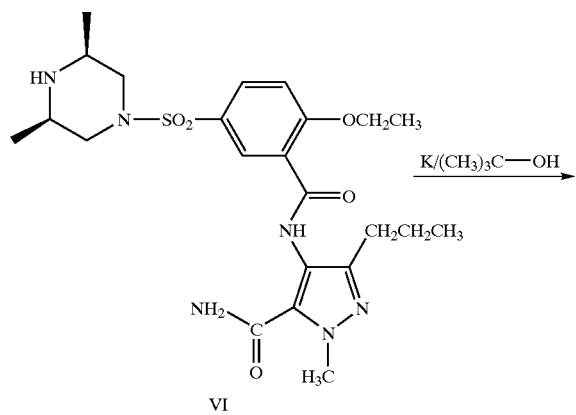

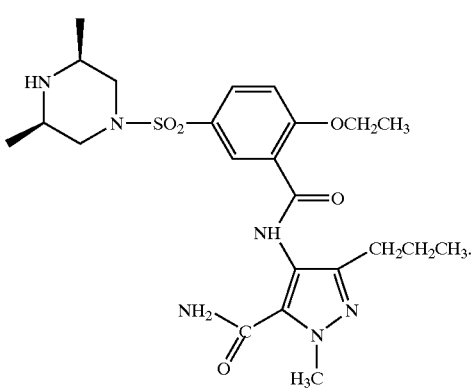

VI

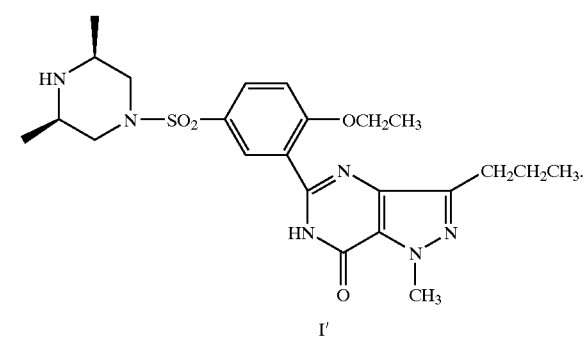

I'

4. A compound of formula (VI), which is 4-[2-ethoxy-5-(cis-2,6-dimethylpiperazin-4-ylsulphonyl)benzamido]-1-methyl-3-n-propyl-pyrazole-5-carboxamide, having the structure as follows:

5. A pharmaceutical composition for treating impotence, comprising a therapeutically effective amount of a compound of formula (I), its pharmaceutically acceptable salts or stereoisomers, as an active component, and a pharmaceutical acceptable carrier.

6. The pharmaceutical composition according to claim 5, wherein the compound of formula (I) is 5-[[2-ethoxy-5-(cis-2,6-dimethylpiperazin-4-ylsulphonyl)phenyl]]-1-methyl-3-n-propyl-7,6-dihydro-1H-pyrazolo[4,3-d]pyrimidin-7-one.

7. A method of treating impotence diseases in a subject comprising administering to the subject a composition comprising a compound of formula (I).

8. The method of claim 7, wherein the compound of formula (I) is 5-[[2-ethoxy-5-(cis-2,6-dimethylpiperazin-4-ylsulphonyl)phenyl]]-1-methyl-3-n-propyl-7,6-dihydro-1H-pyrazolo[4,3-d]pyrimidin-7-one.

* * * * *